United States Patent
Huang et al.

(10) Patent No.: US 9,907,811 B2
(45) Date of Patent: Mar. 6, 2018

(54) CONCENTRATED NATAMYCIN SUSPENSION FORMULATIONS

(71) Applicant: Valent BioSciences Corporation, Libertyville, IL (US)

(72) Inventors: Zhengyu Huang, Buffalo Grove, IL (US); Benjamin A. Belkind, Wilmette, IL (US); Ayyappan Nair, Des Plaines, IL (US); Gregory D. Venburg, Deerfield, IL (US); Robert Fassel, Naches, WA (US); Yong-Ki Kim, Yakima, WA (US)

(73) Assignee: VALENT BIOSCIENCES CORPORATION, Libertyville, IL (US)

(*) Notice: Subject to any disclaimer, the term of this patent is extended or adjusted under 35 U.S.C. 154(b) by 0 days.

(21) Appl. No.: 15/073,952

(22) Filed: Mar. 18, 2016

(65) Prior Publication Data

US 2016/0271158 A1 Sep. 22, 2016

Related U.S. Application Data

(60) Provisional application No. 62/135,316, filed on Mar. 19, 2015.

(51) Int. Cl.
| | |
|---|---|
| A01N 43/653 | (2006.01) |
| A01N 53/00 | (2006.01) |
| A01N 41/10 | (2006.01) |
| A01N 25/04 | (2006.01) |
| A61K 31/7048 | (2006.01) |
| A61K 9/10 | (2006.01) |
| A01N 43/90 | (2006.01) |
| A61K 47/10 | (2017.01) |
| A61K 47/32 | (2006.01) |
| A61K 47/20 | (2006.01) |
| A61K 47/26 | (2006.01) |

(52) U.S. Cl.
CPC ......... *A61K 31/7048* (2013.01); *A01N 43/90* (2013.01); *A61K 9/10* (2013.01); *A61K 47/10* (2013.01); *A61K 47/20* (2013.01); *A61K 47/26* (2013.01); *A61K 47/32* (2013.01)

(58) Field of Classification Search
CPC ...... A01N 53/00; A01N 41/10; A01N 43/653; A01N 25/04; A01N 43/56; A01N 43/54
See application file for complete search history.

(56) References Cited

U.S. PATENT DOCUMENTS

| | | | | |
|---|---|---|---|---|
| 5,468,716 A | * | 11/1995 | Winston | A01N 59/04 424/682 |
| 5,552,151 A | * | 9/1996 | Noordam | A01N 43/90 424/439 |
| 5,667,795 A | | 9/1997 | Fraley et al. | |
| 6,291,436 B1 | | 9/2001 | Ang | |
| 6,559,156 B1 | * | 5/2003 | Dimitrova | A01N 43/54 514/275 |
| 6,576,617 B2 | | 6/2003 | Ang | |
| 2012/0276182 A1 | * | 11/2012 | Baker, Jr. | A61K 9/0014 424/405 |
| 2012/0302559 A1 | * | 11/2012 | Bristow | A01N 43/653 514/229.2 |
| 2013/0309379 A1 | * | 11/2013 | Van Rijn | A01N 43/90 426/532 |

FOREIGN PATENT DOCUMENTS

| | | | |
|---|---|---|---|
| WO | WO 2004/082407 | 9/2004 | |
| WO | WO 2005/074687 | 8/2005 | |
| WO | WO 2007051813 A2 * | 5/2007 | ............. A01N 43/90 |

OTHER PUBLICATIONS

International Search Report issued in corresponding application No. PCT/US2016/023027 dated Jun. 9, 2016.
Tadros, TF, Advances in Colloid and Interface Science, 1993 (46)I-47: Industrial Applications of Dispersions.
Tadros, TF, Advances in Colloid and Interface Science, 1980 (12)141-261: Physical Stability of Suspension concentrates.

* cited by examiner

*Primary Examiner* — Tracy Liu
(74) *Attorney, Agent, or Firm* — Wood, Phillips, Katz, Clark & Mortimer

(57) ABSTRACT

The present invention generally relates to concentrated natamycin suspension formulations for inhibition of fungal growth. Specifically, the present invention relates to stable suspension concentrate formulations comprising from about 25% to about 48% w/w natamycin, from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof, and water. The formulations of the present invention contain natamycin as particles which are on average less than 11 microns in diameter and the formulations have a viscosity of less than 1400 centipoise at 21 degrees Celsius.

20 Claims, No Drawings

CONCENTRATED NATAMYCIN SUSPENSION FORMULATIONS

FIELD OF THE INVENTION

The present invention relates to concentrated natamycin suspension formulations for the inhibition of fungal growth.

BACKGROUND OF THE INVENTION

Natamycin (syn. Pimaricin) is a polyene fungicide that is derived from the soil microorganisms, *Streptomyces natalensis, Streptomyces lydicus*, and *Streptomyces chattanoogensis*. It is commercially produced by fermenting and then lysing *Streptomyces natalensis*. Natamycin is commonly used to deter the growth of fungus on edible solid foods, however, due to its poor solubility in water, it is often difficult to use.

One way the solubility issue has been overcome in the past is by the use of a wettable powder. A wettable powder formulation is a dry, finely ground formulation. In this type of formulation, the active ingredient is combined with a finely ground dry carrier, usually a mineral clay, and with other ingredients that enhance the ability of the powder to be suspended in water. Upon mixing the wettable powder with water, a suspension is formed, which is then applied by a spray technique.

One disadvantage of wettable powders is that the spray liquid must be continuously mixed to prevent settling of insoluble materials. Another disadvantage is that wettable powders and soluble powder formulations tend to produce dust upon handling, such as when pouring, transferring or measuring them. This dust may pose health hazards. Further, powder formulations tend to wet poorly and also solubilize slowly upon addition to water. Powder formulations thus take longer to wet, disperse and solubilize in a tank-mix. Formation of lumps or partially solubilized spray solutions leads to uneven distribution of the natamycin in the tank-mix with the potential for reduced performance. Sometimes, foam in the spray tank caused by spray tank adjuvants can also affect wetting and solubility of wettable and soluble powders. Wettable powder formulations may also leave undesirable insoluble residues both in the tank and on materials in need of treatment.

For many years those of skill in the art have attempted to develop concentrated aqueous natamycin formulations. One challenge is that milling natamycin causes unacceptably high viscosity in most formulations. If natamycin is not milled, however, suspension concentrates are not stable because the natamycin settles out of the formulation. Yet another problem with natamycin formulations is that they are especially susceptible to bacterial growth.

U.S. Pat. No. 5,552,151 suggests natamycin formulations with up to 40% w/w natamycin. This patent fails to provide any formulation examples with such high concentrations of natamycin. Further, the patent states that the most preferred range of natamycin is from 5 to 20%. In addition, this patent fails to teach or suggest how to prevent the natamycin from settling out of a suspension concentrate formulation.

U.S. Pat. Nos. 6,291,436 and 6,576,617 disclose solid natamycin formulations with particles less than 9 microns in diameter. These patents, however, fail to teach or suggest how to overcome the viscosity issues associated with milled natamycin in liquid formulations.

DSM has successfully created suspension concentrate natamycin formulations with concentrations of up to 10% w/w of natamycin (i.e., Zivion A (~4% SC), Zivion P (~4% SC), Delvo® Coat L02101 (~5% SC) and Delvocide L (~10% SC), Delvo is a registered trademark of DSM). While these formulations are successful, there is a need in the art for more concentrated formulations. These formulations will allow for reduced shipping and handling costs.

SUMMARY OF THE INVENTION

In one aspect, the present invention is directed to stable suspension concentrate formulations comprising from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof, and water, wherein the average particle size of the natamycin particles is less than 11 microns in diameter and the formulation has a viscosity of less than 1400 centipoise at 21 degrees Celsius.

In a further aspect, the present invention is directed to methods for inhibiting the growth of human, animal, plant fungal pathogens or food spoilage fungi comprising applying or administering the formulation of the present invention to the human, animal, or plant in need thereof.

In another aspect, the present invention is directed methods for protecting a commodity comprising diluting a suspension concentrate formulation which comprises from about 25% to about 48% w/w natamycin, from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof, and water, and applying the diluted suspension concentrate formulation to the commodity, wherein the natamycin is present as particles in the formulation the particles are on average less than 11 microns in diameter and the formulation has a viscosity of less than 1400 centipoise at 21 degrees Celsius prior to dilution.

DETAILED DESCRIPTION OF THE INVENTION

Applicant unexpectedly discovered that using a specific nonionic and anionic surfactant system, or using specific anionic surfactants, with natamycin particles of reduced size resulted in stable suspension concentrates with natamycin concentrations from about 25% to about 48% w/w. This finding was unexpected because numerous other surfactants, some with similar chemistries, failed to provide satisfactory results (see for example, Example 13 below). Applicant also found that the formulations of the present invention were not acceptable when they only included the tested nonionic surfactants because the viscosity was undesirable or too high (see Example 10 below).

As used herein, "suspension concentrate" refers to a formulation wherein insoluble particles are suspended in liquid or aqueous diluents. A desirable characteristic of suspension concentrates is to have the insoluble particles evenly dispersed within the formulation. A suspension concentrate is not a solution.

Applicant's formulations allow for significant reductions in the costs of processing, packaging, storage, and transportation. The aqueous formulations are also safer and much easier to use than powdered formulations. In addition, all of the components of the formulations are approved by the U.S. Environmental Protection Agency for post-harvest use (see 40 CFR §180.960) and are safe for use in or on food.

In one embodiment, the present invention is directed to stable suspension concentrate formulations comprising from about 25% to about 48% w/w natamycin, from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof, and water, wherein the natamycin is present as particles that on average are less than 11 microns in diameter and the formulation has a viscosity of less than 1400 centipoise at 21 degrees Celsius.

As used herein, "stable" refers to a natamycin suspension concentrate formulation that does not form sediment or exhibit phase separation after being stored for a minimum of 48 hours at 21 degrees Celsius.

The viscosity of a fluid is a measurement of the fluid's resistance to deformation by shear or tensile stress. Fluid viscosity is frequently measured in centipoises (abbreviated as "cps") units with higher numbers correlating to thicker fluids. The viscosity of suspension concentrates must be under 1400 cps to be desirable.

In a preferred embodiment, the formulations contain from about 30% to about 48% w/w natamycin. In a more preferred embodiment, the formulations contain from about 35% to about 48% w/w natamycin.

In yet another embodiment, the formulations contain from about 0.1% to about 3.0% w/w of an anionic surfactant selected from the group consisting of polyelectrolyte polymers, modified styrene acrylic polymers, dioctyl sodium sulfosuccinates, sodium salts of naphthalene sulfonates, and combinations thereof. In a preferred embodiment, the formulations contain from about 0.5% to about 2.5% of an anionic surfactant selected from the group consisting of polyelectrolyte polymers, modified styrene acrylic polymers, dioctyl sodium sulfosuccinates, sodium salts of naphthalene sulfonates, and combinations thereof. In a more preferred embodiment, the formulations contain from about 0.5% to about 1.5% of an anionic surfactant selected from the group consisting of polyelectrolyte polymers, modified styrene acrylic polymers, dioctyl sodium sulfosuccinates, sodium salts of naphthalene sulfonates, and combinations thereof.

In a preferred embodiment, the anionic surfactant is a polyelectrolyte polymer. In a more preferred embodiment, the polyelectrolyte polymer is a sodium lignosulfonate such as Ultrazine NA (available from Borregaard LignoTech).

In another embodiment, the formulations also contain from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof. In a preferred embodiment, the formulations contain from about 0.1% to about 3.0% of a nonionic surfactant selected from the group consisting of polyalkylene oxide block copolymers, polyoxyethylene sorbitan trioleates, polyoxyethylene sorbitol hexaleates, and combinations thereof. In a more preferred embodiment, the formulations contain from about 0.5% to about 2.5% of a nonionic surfactant selected from the group consisting of polyalkylene oxide block copolymers, polyoxyethylene sorbitan trioleates, polyoxyethylene sorbitol hexaleates, and combinations thereof. In a most preferred embodiment, the formulations contain from about 0.5% to about 1.5% of a nonionic surfactant selected from the group consisting of polyalkylene oxide block copolymers, polyoxyethylene sorbitan trioleates, polyoxyethylene sorbitol hexaleates, and combinations thereof.

In a preferred embodiment, the nonionic surfactant is a polyalkylene oxide block copolymer. In a more preferred embodiment, the polyalkylene oxide block copolymer is Atlas™ G-5000 (available from Croda Crop Care).

In another embodiment, the suspension concentrate formulations contain from about 46% to about 75% w/w water. In a more preferred embodiment, the formulations contain from about 64% to about 67% w/w water.

In yet another embodiment, the formulations contain natamycin as particles that are on average less than 11 microns in diameter. In a preferred embodiment, the natamycin particles are on average less than or equal to 9 microns in diameter. In a more preferred embodiment, the natamycin particles are on average less than or equal to 5 microns in diameter. In a most preferred embodiment, the natamycin particles are on average less than or equal to 3 microns in diameter.

In a further embodiment, the formulations contain an antifreeze agent. Examples of suitable antifreeze agents include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, and bisphenols such as bisphenol A.

In a preferred embodiment, the formulations contain from about 1% to about 10% w/w of antifreeze agent. In a more preferred embodiment, the formulations contain from about 3% to about 7% w/w of antifreeze agent. In a most preferred embodiment, the formulations contain from about 4% to about 6% w/w of antifreeze agent.

In a further embodiment, the formulations contain an antifoam agent. Examples of suitable antifoam agents include silicone based antifoam agents, vegetable oils, acetylenic glycols, and high molecular weight adducts of propylene oxide. One preferred antifoam agent is a silicone based anti-foaming agent.

In a preferred embodiment, the formulations contain from about 0.1% to about 5% w/w of an antifoam agent. In a more preferred embodiment, the formulations contain from about 0.5% to about 2% w/w of an antifoam agent. In a most preferred embodiment, the formulations contain from about 0.8% to about 1.2% w/w of an antifoam agent.

In a further embodiment, the formulations contain an antibacterial preservative. Examples of suitable antibacterial preservatives include benzoates and K-sorbate.

In a preferred embodiment, the formulations contain from about 0.01% to about 3% w/w of an antibacterial preservative. In a more preferred embodiment, the formulations contain from about 0.1% to about 2% w/w of an antibacterial preservative. In a most preferred embodiment, the formulations contain from about 0.3% to about 1% w/w of an antibacterial preservative.

In a preferred embodiment, the formulations contain:
about 25% w/w natamycin;
from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof;
from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof; and water,
wherein the natamycin is present as particles that on average are less than 11 microns in diameter and the formulation has a viscosity of less than 1400 centipoise at 21 degrees Celsius.

In a more preferred embodiment, the formulations contain:
about 25% w/w natamycin;
about 1.0% w/w sodium lignosulfonate; and
about 0.5% w/w of a polyalkylene oxide block copolymer, wherein the natamycin is present as particles that on average are less than 11 microns in diameter and the formulation has a viscosity of less than 1400 centipoise at 21 degrees Celsius.

In another embodiment, the present invention is directed to methods for inhibiting the growth of human, animal, plant fungal pathogens or food spoilage fungi comprising applying or administering the formulation of claim 1 to the human, animal, or plant in need thereof.

In a preferred embodiment, the formulations of the present invention are used to inhibit fungal pathogens by administration of the formulations to a human. Suitable uses include treatment of fungal infections in the eyes, mouth or on the skin (fungal keratitis). Preferably, the formulations are administered directly to the area in need of fungal growth inhibition. The formulations are suitable for control of *Candida, Aspergillus, Cephalosporium, Fusarium*, and *Penicillium* growing on a human.

In another preferred embodiment, the formulations of the present invention are used to inhibit fungal pathogens by administration of the formulations to an animal. Suitable uses include treatment of fungal infections in the eyes and the surrounding tissues and ringworm infections. Suitable animals include domesticated animals, such as dogs, cats, cattle and horses. Preferably, the formulations are administered directly to the area in need of fungal growth inhibition. The formulations are suitable for control of *Candida, Aspergillus, Cephalosporium, Fusarium*, and *Penicillium* growing on an animal.

In another preferred embodiment, the formulations of the present invention are used to inhibit fungal pathogens by administration of the formulations to a plant. Suitable plants include commercially cultivated crops.

In a further embodiment, the formulations of the present invention are used to inhibit mold and yeast growth in mushroom growing medium.

In a preferred embodiment, the suspension concentrate formulations that are used for inhibiting the growth of human, animal, plant fungal pathogens or food spoilage fungi further comprise from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

In another embodiment, the present invention is directed to methods for inhibiting fungal growth comprising diluting a suspension concentrate formulation which comprises from about 25% to about 48% w/w natamycin, from about 0.1% to about 10% w/w of an anionic surfactant selected from the group consisting of polyelectrolyte polymers, modified styrene acrylic polymers, dioctyl sodium sulfosuccinates, sodium salts of naphthalene sulfonates, and combinations thereof, and water, and applying the diluted suspension concentrate formulation to a commodity in need of protection from fungal growth, wherein the natamycin is present in the formulation as particles and the particles are on average less than 11 microns in diameter and the formulation has a viscosity of less than 1400 centipoise at 21 degrees Celsius prior to dilution.

In a preferred embodiment, the suspension concentration formulations that are used for inhibiting fungal growth further comprise from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

In an embodiment, the formulations of the present invention are applied to the commodity by dipping, drenching or spraying.

In another embodiment, for formulations are diluted to from about 0.01% to about 5% w/w natamycin before being applied to the commodity. In a preferred embodiment, the formulations are diluted to from about 0.5% to about 2% w/w natamycin before being applied to the commodity.

In an embodiment, the commodities include cheeses, sausages, fruits, vegetables, nuts; cereal rains; animal feed, spices, beverages or other products intended for consumption.

The formulations are suitable for use on a variety of cheeses. The formulations of the present invention may be added to polymer dispersions used to encase the cheese (such as a rind) or the cheese may be dipped or sprayed with the formulations of the present invention. The formulations may also be added to shredded cheeses. Suitable cheeses include Gouda, edam, cheddar, tilsiter, caciotta, fontina, tallegio, montasio, asiago, provolone, pecorino, romano, blue cheeses, and Indian cheeses.

The formulations are suitable for use on a variety of sausages. The formulations of the present invention may be used to dip or spray the outside of the sausages. Alternatively, the sausage casings may be treated before they are filled. The formulations may also be applied to fermented meat products. Suitable sausages include Dutch raw sausages, German raw sausages, and Italian sausages.

The formulations are suitable for use on many types of fruits and vegetables. The formulations of the present invention may be dispersed onto the fruits while they are growing, just prior to harvest, or after harvest. In a preferred embodiment, the formulations of the present invention are dispersed onto the fruits and vegetables after they are harvested. In an alternative embodiment, the formulations of the present invention are dispersed onto the fruits and vegetables while they are still growing on the plants. As used herein, "harvested" or "post-harvest" means that the fruits or vegetables have been removed from the plant they grew on and are no longer growing. As used herein, "dispersion" refers to evenly distributing the formulation over the commodity surface.

As used herein "protecting" refers to reducing the likelihood of fungal pathogens induced rot.

In a preferred embodiment, the suspension concentrate formulation that is applied to the fruits or vegetables also includes from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

Many types of agriculturally or pharmaceutically acceptable diluents may be used to dilute the formulations of the present invention. For example, water, glycerol, hexylene glycol, dipropylene glycol, and polyethylene glycols are all acceptable diluents.

As used herein "fruit" refers to the fleshy tissue associated with a seed of an edible plant. Examples of fruits include citrus fruits, berries, pome fruits (such as apples), stone fruits, melons and bananas.

Examples of citrus fruits include oranges, grapefruits, clementines, mandarins, limes, pomelo, kumquats, and hybrids thereof.

Examples of berries include grapes, aronia berry, bayberry, bearberry, bitberry, blackberry, blueberry, lowbush blueberry, highbush blueberry, buffalo currant, buffaloberry, che, Chilean guava, chokeberry, cloudberry, cranberry, highbush cranberry, black currant, red currant, elderberry, European barberry, gooseberry, grape, edible honeysuckle, huckleberry, jostaberry, Juneberry, lingonberry, maypop, mountain pepper berries, mulberry, muntries, native currant, partridgeberry, phalsa, pincherry, black raspberry, red raspberry, riberry, salal, schisandra berry, sea buckthorn, serviceberry, strawberry, wild raspberry, and cultivars, varieties and hybrids thereof.

Examples of pome fruits include apple, azarole, crabapple, loquat, mayhaw, medlar, pear, Asian pear, quince, Chinese quince, Japanese quince, tejocote, and cultivars, varieties and hybrids thereof.

Examples of stone fruits include apricot, sweet cherry, tart cherry, nectarine, peach, plum, Chicksaw plum, Damson plum, Japanese plum, plumcot, fresh prune, and cultivars, varieties and hybrids thereof.

Examples of melons include citron melons, muskmelons, watermelon, cantaloupe, casaba, crenshaw melon, golden pershaw melon, honeydew melon, honey balls, mango melon, Persian melon, pineapple melon, Santa Claus melon, snake melon and cultivars, varieties and hybrids thereof.

In one embodiment, the diluted formulation is applied to citrus fruits to protect them from sour rot. "Sour rot" refers to a fungal infection caused by *Geotrichum citri-aurantii*.

In another embodiment, the diluted formulation is applied to citrus fruits to protect them from "green mold" or "blue mold." These molds refer to a fungal infection caused by *Penicillium digitatum* or *Penicillium italicum*.

As used herein "vegetable" refers to root and tuber vegetables, bulb vegetables, leafy non-*brassica* vegetables, leafy *brassica* vegetables, succulent or dried legumes, fruiting vegetables, and cucurbit vegetables.

In a preferred embodiment, the diluted formulation is applied by dipping, drenching, or spraying the commodities with and without coating waxes.

In another embodiment, the formulations are diluted to a concentration of from about 0.01% to about 5% w/w natamycin before being applied to the commodities. In a preferred embodiment, the formulations are diluted to a concentration of from about 0.5% to about 2% w/w natamycin before being applied to the commodities.

Examples of beverages include juices, beer, wine, soft drinks, iced tea and fruit yogurts. Suitable juices include fruit juices and blend thereof, including lemonade and orange juices.

The formulations of the present invention could also include the fungicides lucensomycin, nystatin, amphotericin-B or combinations thereof.

The formulations of the present invention specifically exclude thickening agents and anti-caking materials.

The formulations of the present invention specifically exclude lactose powder and sodium chloride.

The formulations of the present invention specifically exclude polyoxyethylene alcohol nonionic surfactants, polyoxyethylene lauryl ether nonionic surfactants, and polyoxyethylene cetyl ether nonionic surfactants.

The formulations of the present invention may be applied so that the natamycin concentration is less than 1 ppm or greater than 5 ppm.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The disclosed embodiments are simply exemplary embodiments of the inventive concepts disclosed herein and should not be considered as limiting, unless so stated.

The following examples are intended to illustrate the present invention and to teach one of ordinary skill in the art how to make and use the invention. They are not intended to be limiting in any way.

EXAMPLES

Applicant used natamycin in the form of Technical Grade Active Ingredient ("TGAI") when preparing the formulations of the present invention. The percent natamycin in the technical grade typically ranges between 80% and 99% w/w. Variations in the activity of natamycin in the TGAI should be accounted for by decreasing or increasing the amount of diluent in producing the natamycin formulation of the desired concentration. This is standard practice within the guidelines of US Environmental Protection Agency per 40 C.F.R. §158.175(b)(2).

Applicant prepared the following natamycin suspension concentrate formulations as follows unless otherwise noted. Natamycin was processed until it was on average below 11 microns in diameter. The other formulation components were added and the formulation was stirred until the natamycin particles fully dispersed. "Q.s." refers to a sufficient quantity of water to reach the proper % w/w of the formulation.

Example 1

Concentrated 25% Natamycin Suspension Formulations

TABLE 1

| | Component (all in % wt/wt) | | | | | |
| --- | --- | --- | --- | --- | --- | --- |
| | 1A | 1B | 1C | 1D | 1E | 1F |
| Natamycin technical powder | 25 | 25 | 25 | 25 | 25 | 25 |
| Polyalkylene oxide block copolymer nonionic surfactant | 0.5-2.5 | — | — | 0.5-2.5 | 0.5-2.5 | 0.5-2.5 |
| Polyoxyethylene sorbitan trioleate nonionic surfactant | — | 0.5-2.5 | — | — | — | — |
| Polyoxyethylene sorbitan hexaoleate nonionic surfactant | — | — | 0.5-2.5 | — | — | — |
| Sodium lignosulfonate (polyelectrolyte polymer anionic surfactant) | 0.5-1.5 | 0.5-1.5 | 0.5-1.5 | — | — | — |
| Modified styrene acrylic polymer anionic surfactant | — | — | — | 0.5-1.5 | — | — |
| Dioctyl sodium sulfosuccinates anionic surfactant | — | — | — | — | 0.5-1.5 | — |
| Sodium salts of naphthalene sulfonate anionic surfactant | — | — | — | — | — | 0.5-1.5 |
| Antifreeze agent | 5 | 5 | 5 | 5 | 5 | 5 |
| Antibacterial preservative | 0.3-1 | 0.3-1 | 0.3-1 | 0.3-1 | 0.3-1 | 0.3-1 |
| Antifoam agent | 1 | 1 | 1 | 1 | 1 | 1 |
| Water | q.s. | q.s. | q.s. | q.s. | q.s. | q.s. |
| | 100% | 100% | 100% | 100% | 100% | 100% |

Example 2

Additional Concentrated 25% Natamycin Suspension Formulations

TABLE 2

| Component (all in % wt/wt) | 2A | 2B |
| --- | --- | --- |
| Natamycin technical powder | 25 | 25 |
| Polyalkylene oxide block copolymer nonionic surfactant | — | 0.5 |
| Sodium lignosulfonate (polyelectrolyte polymer anionic surfactant) | 1.0 | 1.0 |
| Antifreeze agent | 5 | 5 |
| Antibacterial preservative | 0.3-1 | 0.3-1 |
| Antifoam agent | 1 | 1 |
| Water | q.s. | q.s. |
| | 100% | 100% |

Example 3

Concentrated 35% Natamycin Suspension Formulation

TABLE 3

| Component | % wt/wt |
| --- | --- |
| Natamycin technical powder | 35 |
| Antifreeze agent | 5 |
| Polyalkylene oxide block | 0.5-2.5 |

TABLE 3-continued

| Component | % wt/wt |
|---|---|
| copolymer nonionic surfactant | |
| Sodium lignosulfonate anionic surfactant | 0.5-1.5 |
| Antibacterial preservative | 0.3-1 |
| Antifoam agent | 1 |
| Water | q.s. |
| | 100% |

Example 4

Concentrated 40% Natamycin Suspension Formulation

TABLE 4

| Component | % wt/wt |
|---|---|
| Natamycin technical powder | 40 |
| Antifreeze agent | 5 |
| Polyalkylene oxide block copolymer nonionic surfactant | 0.5-2.5 |
| Sodium lignosulfonate anionic surfactant | 0.5-1.5 |
| Antibacterial preservative | 0.3-1 |
| Antifoam agent | 1 |
| Water | q.s. |
| | 100% |

Example 5

Concentrated 45% Natamycin Suspension Formulation

TABLE 5

| Component | % wt/wt |
|---|---|
| Natamycin technical powder | 45 |
| Antifreeze agent | 5 |
| Polyalkylene oxide block copolymer nonionic surfactant | 0.5-2.5 |
| Sodium lignosulfonate anionic surfactant | 0.5-1.5 |
| Antibacterial preservative | 0.3-1 |
| Antifoam agent | 1 |
| Water | q.s. |
| | 100% |

Example 6

Concentrated 46% Natamycin Suspension Formulation

TABLE 6

| Component | % wt/wt |
|---|---|
| Natamycin technical powder | 46 |
| Antifreeze agent | 5 |
| Polyalkylene oxide block copolymer nonionic surfactant | 0.5-2.5 |

TABLE 6-continued

| Component | % wt/wt |
|---|---|
| Sodium lignosulfonate anionic surfactant | 0.5-1.5 |
| Antibacterial preservative | 0.3-1 |
| Antifoam agent | 1 |
| Water | q.s. |
| | 100% |

Example 7

Concentrated 47.5% Natamycin Suspension Formulation

TABLE 7

| Component | % wt/wt |
|---|---|
| Natamycin technical powder | 47.5 |
| Antifreeze agent | 5 |
| Polyalkylene oxide block copolymer nonionic surfactant | 0.5-2.5 |
| Sodium lignosulfonate anionic surfactant | 0.5-1.5 |
| Antibacterial preservative | 0.3-1 |
| Antifoam agent | 1 |
| Water | q.s. |
| | 100% |

Comparative Example 8

Concentrated 50% Natamycin Suspension Formulation

TABLE 8

| Component | % wt/wt |
|---|---|
| Natamycin technical powder | 50 |
| Antifreeze agent | 5 |
| Polyalkylene oxide block copolymer nonionic surfactant | 0.5-2.5 |
| Sodium lignosulfonate anionic surfactant | 0.5-1.5 |
| Antibacterial preservative | 0.3-1 |
| Antifoam agent | 1 |
| Water | q.s. |
| | 100% |

Example 9

Viscosity Studies

Applicant tested the viscosity of the formulations of Examples 2A, 2B, 5, 6, 7 and Comparative Example 8. This study was conducted using standard procedures known and accepted by those of skill in the art. The results of this study can be seen below in Table 9.

TABLE 9

| Formulation | % w/w Natamycin | Viscosity (cps) |
| --- | --- | --- |
| Example 2A | 25 | 1080 |
| Example 2B | 25 | 340 |
| Example 5 | 45 | 867 |
| Example 6 | 46 | 940 |
| Example 8 | 47.5 | 1375 |
| Comparative Example 7 | 50 | 2225 |

As can be seen in Table 9 above, the compositions of Examples 2A, 2B, 5, 6, and 7 have viscosities that render the compositions suitable for use as a suspension concentrate for administration to plants, animals, or humans (viscosities were less than 1400 cps) and for other uses which has similar viscosity restrictions. In contrast, the 50% natamycin formulation of Comparative Example 8 was unacceptably thick (2225 cps). Accordingly, Applicant determined that the formulations at concentrations of up to 48% natamycin are suitable.

Example 10

Additional Viscosity Studies

Applicant tested the viscosity of 25% natamycin suspension concentrate formulations with 2% of different nonionic surfactants. This study was conducted using standard procedures known and accepted by those of skill in the art. The results of this study can be seen below in Table 10.

TABLE 10

| Surfactant (2% w/w) | Viscosity (cps) |
| --- | --- |
| Control, water added instead of surfactant | 2810 |
| Control, anionic surfactant, sodium lignosulfonate | 782 |
| Polyoxyethylene (20) sorbitan monolaurate, nonionic surfactant | 2010 |
| Acrylic copolymer, nonionic surfactant | 1850 |
| Polyoxyethylene (20) oleyl ether, nonionic surfactant | 1720 |
| Polyalkylene oxide block copolymer, nonionic surfactant | 2014 |
| Polyoxyethylene (20) sorbitan trioleate, nonionic surfactant | 2960 |
| Polyoxyethylene (40) sorbitol hexaoleate, nonionic surfactant | 7580 |

As seen in Table 10 above, all of the six nonionic surfactants tested failed to provide the desirable viscosity (~1400 cps or lower) when used alone in a 25% suspension concentrate natamycin formulations. In contrast, the anionic surfactant, sodium lignosulfonate, used alone provided the desirable viscosity in a 25% suspension concentrate natamycin formulation.

Example 11

Particle Size Stability Study

Applicant tested how the particle size of natamycin impacted the stability of suspension concentrate formulations. This study was conducted using standard procedures known and accepted by those of skill in the art. A 25% natamycin formulation with natamycin particles with average (D(4,3)) diameters of 11 microns was compared with a 25% natamycin formulation with natamycin particles with average diameters of 3 microns. The results of this study can be seen below in Table 11.

TABLE 11

| Average D(4,3) Natamycin Particle Diameter (microns) | Initial | 30 mins | 4 hours | 24 hours | 48 hours |
| --- | --- | --- | --- | --- | --- |
| 11 | Homogenous | Some sedimentation | 16% sedimentation | 48% sedimentation | N/A |
| 3 | Homogenous | Homogenous; no sedimentation or separation | Homogenous; no sedimentation or separation | Homogenous; no sedimentation or separation | Homogenous; no sedimentation or separation |

As can be seen in Table 11 above, the formulation with the smaller natamycin particles was homogenous and did not exhibit sedimentation or separation even after 48 hours. In contrast, a similar formulation with larger natamycin particles formed sediment after only 30 minutes. By 24 hours, there was excessive sedimentation that required 10 inversions to re-suspend.

This study shows that particle size is an important aspect of Applicant's suspension concentrate formulations.

Example 12

Another Particle Size Stability Study

Applicant tested how particle sizes of 9 microns impacts the stability of the suspension concentrate formulations. The study used standard procedures known and accepted by those of skill in the art. A 25% natamycin formulation with natamycin particles with average (D(4,3)) diameters of 11 microns was compared with a 25% natamycin formulation with natamycin particles with average diameters of 9 microns. The results of this study can be seen in Table 12 below.

TABLE 12

| Average D(4,3) Natamycin Particle Diameter (microns) | Initial | 30 mins | 4 hours | 24 hours | 48 hours |
|---|---|---|---|---|---|
| 11 | Homogenous | Some sedimentation | 16% sedimentation | 48% sedimentation | N/A |
| 9 | Homogenous | Homogenous | Homogenous | 1.4% Sedimentation | 2.8% Sedimentation |

As can be seen in Table 12 above, the formulation with the smaller natamycin particles was homogenous and did not exhibit sedimentation or separation after 4 hours. In contrast, a similar formulation with larger natamycin particles formed sediment after only 30 minutes. By 24 hours, there was excessive sedimentation that required 10 inversions to resuspend.

This study shows that particle size is an important aspect of Applicant's suspension concentrate formulations.

Example 13

Testing of Alternative Nonionic and Anionic Surfactants

While developing the formulations of the present invention, Applicant also tested numerous other surfactant combinations that failed to show synergy. A summary of these results is below in Table 13.

Method

Inoculum Preparation

One isolate each of *Botrytis cinerea* (A810) and *Penicillium expansum* (A003) was recovered from stock culture collections saved in silica-gel at 4° C. After 3 days of growth on potato dextrose agar (PDA), *B. cinerea* was sporulated under a 12-fluorescent light for 2 weeks. A conidial suspension was made by adding 20 ml of sterile water and gently removing the conidia with a sterile plastic loop. A spore suspension was filtered through two layers of cheesecloth. The final concentration was adjusted to $1 \times 10^5$ conidia/ml with a hemacytometer. For *P. expansum*, dry conidia were transferred into 5 ml of sterile water containing 0.01% Tween 20® (Tween is a registered trademark of Croda Americas LLC) by a plastic loop after wetting in the Tween 20® water. After vortexing vigorously, spores were diluted in 0.01% Tween 20® water and adjusted to $1 \times 10^4$ conidia/ml.

TABLE 13

| | Nonionic Surfactants | | | | | | |
|---|---|---|---|---|---|---|---|
| Anionic Surfactants | Polyoxyethylene alcohols | Polyoxyethylene lauryl ethers | Polyoxyethylene cetyl ethers | Acrylic copolymers | Polyalkylene oxide block copolymers | Polyoxyethylene sorbitan trioleates | Polyoxyethylene sorbitan hexaoleates |
| Polyelectrolyte polymers | No synergy | No synergy | No synergy | No synergy | Synergy | Synergy | Synergy |
| Modified styrene acrylic polymers | No synergy | No synergy | No synergy | No synergy | Synergy | Synergy | Synergy |
| Doctyl sodium sulfosuccinates | No synergy | No synergy | No synergy | No synergy | Synergy | Synergy | Synergy |
| Sodium salts of naphthalene sulfonates | No synergy | No synergy | No synergy | No synergy | Synergy | Synergy | Synergy |

As illustrated in Table 13, Applicant was unable to predict which surfactants would exhibit synergy and allow for large amounts (up to 48% w/w) of natamycin to be suspended while providing the desirable viscosity of the formulations. Applicant tried polyoxyethylene alcohol nonionic surfactants, polyoxyethylene lauryl ether nonionic surfactants, polyoxyethylene cetyl ether nonionic surfactants, and acrylic copolymer nonionic surfactants without success. In contrast, the claimed surfactants all provided suitable formulations that were stable and had low viscosity.

Example 14

Control of Gray Mold and Blue Mold of Apple

Formulation 2B from Table 2, above, was tested for its ability to control gray mold and blue mold of apple.

Fruit Inoculation

Organic 'Red Delicious' apples that were washed in hypochlorite and packed in a commercial apple packinghouse were purchased. The apples were incubated at ambient temperature at least 12 hours prior to the experiment. The apples were then wound-inoculated by adding 10 µl of the inoculum suspensions prepared as above into a wound created with a finished nail-head (3×4 mm). The apples were incubated at room temperature for 4 hours before fungicide treatments.

Treatment

The apples were placed in a polyethylene mesh bag and dipped in fungicide solutions for 30 seconds. Fungicides tested were Formulation 2B of the instant invention, Zivion® M (10.34% natamycin, Zivion is a registered trademark of and available from DSM IP Assets B.V. of the Netherlands) and Shield-Brite® FDL 230SC (20.4% fludioxonil, Shield Brite is a registered trademark of Pace International, LLC; Shield-Brite® FDL 230SC is available from Pace International, LLC). After treatments, the apples were placed on fiber apple trays in a cardboard box, and stored at 4° C. in air. Apples dipped in water were used as a control. Twenty apples per replicate and 4 replicates per treatment were used. At least 1-Kg apples per treatment were treated and used for fruit residue analysis. Liquid solutions were sampled and analyzed for natamycin concentrations.

Data Analysis

The evaluations were conduct after 6 weeks of cold storage. The percent of decay incidences in the dip treatments were arcsine-transformed and analyzed with SAS PROC GLM (version 9.1; SAS Institute) to compare the treatments. Means were separated by Fisher's protected least significant difference at P=0.05.

Results

This study was conducted to determine the effectiveness of natamycin formulations of the present invention in controlling gray mold and blue mold of apple by aqueous dip application.

In general, Formulation 2B of the instant invention showed better performance than Zivion® M in controlling both gray mold and blue mold of apples when applied by an aqueous dip. See Tables 14 & 15, respectively. Formulation 2B was equally effective as fludioxonil 180 ppm against both pathogens when applied at 750 ppm or 1,000 ppm. All 3 rates of Formulation 2B were equally effective to each other in controlling gray mold (Table 14), whereas 500-ppm Formulation 2B was less effective than 750 ppm or 1,000 ppm in controlling blue mold (Table 15).

Regardless of the rates, apples treated with Zivion® M showed higher decay incidences of gray mold and blue mold than those treated with Formulation 2B. Surprisingly, the difference in decay rate cannot be explained solely by the 2.5 times difference in the amount of natamycin between Formulation 2B and Zivion® M. First, Formulation 2B showed more than a 2.5 times reduction in mold over Zivion® M. Specifically, at an application rate of 1,000 ppm Formulation 2B resulted in 3.5 times less gray mold than application of the same rate of Zivion® M. See Table 14. At an application rate of 750 ppm Formulation 2B resulted in 4.3 times less gray mold than Zivion® M. At an application rate of 750 ppm Formulation 2B resulted in 3.68 times less blue mold than Zivion® M.

Secondly, the liquid concentrations and fruit residues of natamycin were very similar between Formulation 2B and Zivion® M in both trials. See Tables 14 & 15. Thus, the natamycin formulations of the present invention show unexpected results over commercially available natamycin formulations.

Further research will be needed to investigate why the natamycin formulations performed differently on the control of gray mold and blue mold in apples.

TABLE 14

| Treatment | Target rate (ppm) | Measured natamycin (ppm) Solution | Fruit | Gray mold (%) |
|---|---|---|---|---|
| Water |  | 0 | 0.00 | 88.8 a* |
| Formulation 2B | 1000 | 1076 | 2.11 | 2.5 ef |
|  | 750 | 801 | 1.75 | 3.8 def |
|  | 500 | 528 | 1.25 | 7.5 cde |

TABLE 14-continued

| Treatment | Target rate (ppm) | Measured natamycin (ppm) Solution | Fruit | Gray mold (%) |
|---|---|---|---|---|
| Zivion® M | 1000 | 1089 | 2.34 | 8.8 bcd |
|  | 750 | 803 | 1.89 | 16.3 b |
|  | 500 | 544 | 1.18 | 13.8 bc |
| Shield-Brite® FDL 230SC | 180 | 171 | 0.43 | 1.3 f |

*Values with a common letter are not significantly different according to the analysis of variance and least significant difference at P = 0.05.

TABLE 15

| Treatment | Target rate (ppm) | Measured natamycin (ppm) Solution | Fruit | Blue mold (%) |
|---|---|---|---|---|
| Water |  | 0 | 0.00 | 95.0 a* |
| Formulation 2B | 1000 | 1006 | 2.21 | 21.3 c |
|  | 750 | 751 | 1.60 | 16.3 c |
|  | 500 | 497 | 1.24 | 42.5 b |
| Zivion® M | 1000 | 1093 | 2.43 | 55.0 b |
|  | 750 | 784 | 1.65 | 60.0 b |
|  | 500 | 519 | 1.18 | 60.0 b |
| Shield-Brite® FDL 230SC | 180 | 156 | 0.38 | 8.8 c |

*Values with a common letter are not significantly different according to the analysis of variance and least significant difference at P = 0.05.

Example 15

Control of Postharvest Diseases in Citrus

Formulation 2B from Table 2, above, was tested for its ability to control green mold of lemons and oranges and sour rot in lemons.

Methods

Fruit Preparation

Two bins each of light green 'Eureka' lemons and 'Washington navel' oranges were harvested Dec. 15, 2014 at the University of California, Lindcove Research and Extension Center (UC-LREC). An additional bin of yellow, more mature 'Eureka' lemons was provided by Pace International, LLC that was harvested from District 1 region of California. All fruit was pressure washed at 100 psi for 20 seconds in 200 ppm chlorine, then divided into totes of 150 fruit each. The totes were placed at 20° C. for 36 hours before inoculation from 6 to 9 P.M. on Dec. 17, 2014.

Inoculum Preparation

One isolate each of *Penicillium digitatum* (A857; fungicide sensitive) and *Geotrichum citri-aurantii* (A005) was used for this study. Fungal cultures were reactivated from silica-gel stocks and grown on PDA. The plate was flooded with 0.01% Tween® 20 solution for *P. digitatum* and sterile water for *G. citri-aurantii*, and conidia were scraped off with a sterile loop. The final concentrations were adjusted to $5 \times 10^5$ and $5 \times 10^7$ spores/ml for *P. digitatum* and *G. citri-aurantii*, respectively. Both solutions were kept in an ice chest until they were used.

Fruit Inoculation

Lemons and oranges with no postharvest fungicide treatments were used. For *P. digitatum* and *G. citri-aurantii* inoculation, a sterile steel rod (1×2 mm) was dipped in the inoculum suspension and fruit was wound-inoculated by making a single puncture on equatorial surface 12 to 16 hours before treatments were applied. The pallets of lemons inoculated with *G. citri-aurantii* were covered with a plastic bag to maintain high humidity. After treatment, fruits were placed on fruit cavity trays in cartons and placed in the large temperature-controlled room at UC-LREC at 50° F.

Fungicides tested were Formulation 2B of the instant invention, Shield-Brite® FDL 230SC, Mentor® (45% propiconazole; Mentor is a registered trademark and available from Syngenta Participations AG), Shield-Brite® TBZ 500D (42.3% thiabendazole; available from Pace International, LLC), Shield-Brite® Penbotec® 400SC (37.14% pyrimentanil; Penbotec is a registered trademark of Johnson & Johnson Corporation; Shield-Brite® Penbotec® 400SC is available through Pace International, LLC), PacRite® Fungaflor 75 WSG (100% imazalil; PacRite® is a registered trademark of Pace International, LLC; PacRite® Fungaflor 75 WSG is available through Pace International, LLC), and Graduate A+® (fludioxonil in combination with azoxystrobin; Graduate A+ is a registered trademark of and available through Syngenta Participations AG).

Application Method

Fungicides were applied by recirculating flooder with two troughs and a residence time of about 7 seconds with a system volume of 75 gallons and a flow rate of 50 gal/minute with or without an addition of coating wax, except that thiabendazole was applied by spraying with a pack wax in wax cabinet with dryer at 120° F. ("pack wax").

Treatment

1. Green Mold on Lemons

Fruit were inoculated 12-16 hours before treatment at 68° F. with *P. digitatum*. Treatments were applied to 3 sets of 45 lemons from 9 A.M. to 2 P.M. on Dec. 18, 2014 followed by storage at 50° F. until Jan. 5, 2015 when they were examined for decay development.

2. Green Mold on Oranges

Fruit were inoculated 12-16 hours before treatment at 68° F. with *P. digitatum*. Treatments applied to 3 sets of 45 oranges from 9 A.M. to 2 P.M. on Dec. 18, 2014 followed by storage at 50° F. until Jan. 5, 2015, then 3 days at 72° F., then 4 days at 50° F. that ended on Jan. 12, 2015 when they were examined.

3. Sour Rot on Lemons

Fruit were inoculated 12-16 hours before treatment at 68° F. with *G. citri-aurantii*. Treatments applied to 3 sets of 45 lemons from 9 A.M. to 2 P.M. on Dec. 18, 2014 followed by storage at 50° F. until Jan. 5, 2015, then 3 days at 72° F., then 4 days at 50° F. that ended on Jan. 12, 2015 when they were examined.

Data Analysis

The percent of decay incidences were arcsine-transformed and analyzed with SAS PROC GLM (version 9.1; SAS Institute) to compare the treatments. Means were separated by Fisher's protected least significant difference at P=0.05. The mean separation via Fisher's Protected $LSD_{0.05}$ in Table 16 below was 3.4 for green mold on lemons, 13.6 for green mold on oranges and 5.8 for sour rot on lemons.

Results

This study was conducted to determine the effectiveness of natamycin formulations of the present invention in controlling green mold of lemons and oranges and sour rot of lemons by aqueous dip or flooder application.

In general, application of Formulation 2B of the present invention resulted in significantly less green mold and sour rot than control. See Table 16. Further, application of Formulation 2B resulted in statistically less green mold and sour rot than commercial fungicides. Specifically, application of Formulation 2B via a flooder at 500 ppm and via a flooder at 1,000 ppm with storage wax resulted in statistically less green mold on lemons than 2,000 ppm Shield-Brite® TBZ 500D applied via a spray with pack wax. See Table 16. Application of Formulation 2B via a flooder at 500 ppm and 1,000 ppm and via dip at 500 ppm resulted in statistically less green mold on oranges than 300 ppm Shield-Brite® FDL 230SC applied via a flooder. See Table 16. Finally, application of Formulation 2B via a flooder at 500 ppm and 1,000 ppm resulted in statistically less green mold on oranges than 3,500 ppm Shield-Brite® TBZ 500D applied via a spray with pack wax. See Table 16. In conclusion, Formulation 2B of the present invention is capable of controlling green mold and sour rot on lemons and oranges as well as, and in some examples better than, commercially available fungicides.

TABLE 16

| Treatment | Target rate (ppm) | Application Method | Wax | Green mold (%) Lemons | Green mold (%) Oranges | Sour rot (%) Lemons |
|---|---|---|---|---|---|---|
| Water | | | | 100 | 96.3 | 37.8 |
| Formulation 2B | 500 | Flooder | No | 0.7 | 24.7 | 6 |
| Formulation 2B | 500 | Dip 30 sec | No | 4.4 | 26.1 | 4.4 |
| Formulation 2B | 1000 | Flooder | No | 4.5 | 22.4 | 14.7 |
| Formulation 2B | 1000 | Flooder | Storage wax, no fungicide | 1.9 | 39.1 | 10 |
| Formulation 2B | 1000 | Flooder | Pack wax, no fungicide | 3.4 | 40.8 | 14.2 |
| Formulation 2B | 1000 | Dip 30 sec | No | 3 | 43.7 | 2.9 |
| Shield-Brite ® FDL 230SC | 180 | Flooder | No | 1.3 | 29.1 | — |
| Shield-Brite ® FDL 230SC | 300 | Flooder | No | 2.2 | 46.1 | — |
| PacRite ® Fungaflor 75 SWG | 500 | Flooder | No | 0.6 | 11.4 | — |
| Shield-Brite ® Penbotec ® 400SC | 500 | Flooder | No | 1.5 | 12.3 | — |
| Shield-Brite ® TBZ 500D | 3500 | Wax | Pack wax, fungicide | 5.7 | 38.9 | — |

TABLE 16-continued

| Treatment | Target rate (ppm) | Application Method | Wax | Green mold (%) | | Sour rot (%) |
|---|---|---|---|---|---|---|
| | | | | Lemons | Oranges | Lemons |
| Formulation 2B + Shield-Brite ® FDL 230SC | 500 + 180 | Flooder | No | 0 | 21.1 | — |
| Formulation 2B + Shield-Brite ® FDL 230SC | 1000 + 300 | Flooder | No | 1.3 | 41.3 | — |
| Formulation 2B + PacRite ® Fungaflor 75 SWG | 1000 + 500 | Flooder | No | 0 | 11 | — |
| Formulation 2B + Shield-Brite ® Penbotec ® 400SC | 1000 + 500 | Flooder | No | 0 | 10.4 | — |
| Formulation 2B + Shield-Brite ® TBZ 500D | 1000 + 3500 | 2B, flooder | Pack wax, fungicide | 1.5 | 8 | — |
| Graduate A+ ® | 300 + 300 | Flooder | No | 0 | 22 | — |
| Mentor ® | 540 | Flooder | No | — | — | 2.8 |
| Mentor ® | 540 | Dip 30 sec | No | — | — | 0.7 |

The invention claimed is:

1. A stable suspension concentrate formulation for inhibition of fungal growth comprising:
from about 25% to 48% w/w of solid natamycin;
from about 0.1% to about 10% w/w of sodium lignosulfonate; and
water,
wherein the natamycin is present as particles that on average are from 3 to 9 microns in diameter, the formulation has a viscosity of less than 1400 centipoise at 21 degrees Celsius, and the formulation is stable for at least 4 hours at 21 degrees Celsius.

2. The formulation of claim 1 further comprising from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

3. The formulation of claim 1 wherein the formulation contains from about 30% to 48% w/w of solid natamycin.

4. The formulation of claim 3 wherein the formulation contains from about 35% to 48% w/w of solid natamycin.

5. The formulation of claim 1 further comprising from about 0.1% to 3.0% w/w nonionic surfactant.

6. The formulation of claim 2 wherein the formulation contains from about 0.1% to 3.0% w/w nonionic surfactant.

7. The formulation of claim 1 wherein the sodium lignosulfonate is at a concentration from about 0.5% to about 1.5% w/w.

8. The formulation of claim 7 wherein the sodium lignosulfonate is at a concentration of about 1.0% w/w.

9. The formulation of claim 2 wherein the nonionic surfactant is at least one polyalkylene oxide block copolymer.

10. The formulation of claim 1 comprising from about 46% to about 75 w/w water.

11. A stable suspension concentrate formulation for inhibition of fungal growth comprising:
from about 25% to 48% w/w of solid natamycin;
about 1% w/w of sodium lignosulfonate; and
water,
wherein the natamycin is present as particles that on average are from 3 to 9 microns in diameter, the formulation has a viscosity of less than 1400 centipoise at 21 degrees Celsius, and the formulation is stable for at least 4 hours at 21 degrees Celsius.

12. The formulation of claim 11 further comprising from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

13. The formulation of claim 12 wherein:
the nonionic surfactant is a polyalkylene oxide block copolymer at a concentration of about 0.5% w/w.

14. A method for inhibiting the growth of human, animal, or plant fungal pathogens comprising applying or administering the formulation of claim 1 to a human, animal, or plant in need thereof.

15. The method of claim 14 wherein the suspension concentrate formulation further comprises from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

16. A method of inhibiting fungal growth comprising:
(a) diluting a suspension concentrate formulation which comprises from about 25% to 48% w/w of solid natamycin, from about 0.1% to about 10% w/w of sodium lignosulfonate, and water; and
(b) applying the diluted suspension concentrate formulation to a commodity in need of protection from fungal growth,
wherein the solid natamycin is present as particles that on average are from 3 to 9 microns in diameter, the formulation has a viscosity of less than 1400 centipoise at 21 degrees Celsius prior to dilution, and the formulation is stable for at least 4 hours at 21 degrees Celsius.

17. The method of claim 16 wherein the suspension concentrate formulation further comprises from about 0.1% to about 10% w/w of a nonionic surfactant selected from the group consisting of polyalkylene oxide block copolymers, polyoxyethylene sorbitan trioleates, polyoxyethylene sorbitol hexaleates, and combinations thereof.

18. The method of claim 16 wherein the diluted formulation is applied by dipping, drenching, or spraying.

19. The method of claim 16 wherein the formulation is diluted to a concentration of from about 0.01% to about 5 w/w of solid natamycin before being applied to the commodity.

20. The method of claim 19 wherein the formulation is diluted to a concentration of from about 0.5% to about 2% w/w of solid natamycin before being applied to the commodity.

* * * * *